US011806002B2

(12) United States Patent
Farley

(10) Patent No.: US 11,806,002 B2
(45) Date of Patent: Nov. 7, 2023

(54) RETRACTOR SYSTEM AND RETRACTOR ARM WITH DETACHABLE HANDLE

(71) Applicant: Thompson Surgical Instruments, Inc., Traverse City, MI (US)

(72) Inventor: Daniel K. Farley, Traverse City, MI (US)

(73) Assignee: THOMPSON SURGICAL INSTRUMENTS, INC., Traverse City, MI (US)

( * ) Notice: Subject to any disclaimer, the term of this patent is extended or adjusted under 35 U.S.C. 154(b) by 94 days.

(21) Appl. No.: 17/163,882

(22) Filed: Feb. 1, 2021

(65) Prior Publication Data
US 2022/0240915 A1 Aug. 4, 2022

(51) Int. Cl.
*A61B 17/02* (2006.01)
*A61B 90/50* (2016.01)
*A61B 90/57* (2016.01)
*A61B 17/00* (2006.01)

(52) U.S. Cl.
CPC ............. *A61B 17/02* (2013.01); *A61B 90/50* (2016.02); *A61B 2017/0046* (2013.01); *A61B 2090/571* (2016.02)

(58) Field of Classification Search
CPC . A61B 17/02; A61B 17/0206; A61B 17/0281; A61B 17/0293; A61B 90/50; A61B 2090/571; A61B 2017/0046
See application file for complete search history.

(56) References Cited

U.S. PATENT DOCUMENTS

| 3,749,088 A | 7/1973 | Kohlmann |
| 4,143,652 A * | 3/1979 | Meier .................. F16M 13/022 600/230 |
| 4,971,038 A | 11/1990 | Farley |

(Continued)

FOREIGN PATENT DOCUMENTS

| EP | 1269922 | 1/2013 |
| ES | 2272170 | 4/2007 |

(Continued)

OTHER PUBLICATIONS

International Preliminary Report on Patentability for PCT/US2018/047164, dated Apr. 2, 2020, 19 pages.

(Continued)

*Primary Examiner* — Tracy L Kamikawa
(74) *Attorney, Agent, or Firm* — McAndrews, Held & Malloy, Ltd.

(57) ABSTRACT

A retractor system includes a mounting assembly, an articulated arm coupled to the mounting assembly, a retractor connector coupled to the articulated arm, and a handle. The articulated arm includes arm segments and joints that permit articulation of the arm segments. The retractor connector includes an attachment port adapted to receive an attachment post of a retractor blade. A handle mount includes a tab and a pedestal that affixes the tab to an arm segment of the articulated arm. The handle includes an attachment portion and a rod. The attachment portion includes a slot configured to receive the tab of the handle mount. The rod engages the tab of the handle mount and secures the handle to the handle mount when advanced through the attachment portion and into the slot.

18 Claims, 8 Drawing Sheets

(56) References Cited

U.S. PATENT DOCUMENTS

| | | | |
|---|---|---|---|
| 5,520,610 A | 5/1996 | Giglio et al. | |
| 5,902,233 A | 5/1999 | Farley et al. | |
| 5,931,777 A | 8/1999 | Sava | |
| 5,984,865 A | 11/1999 | Farley et al. | |
| 5,984,867 A | 11/1999 | Deckman et al. | |
| 6,036,641 A | 3/2000 | Taylor et al. | |
| 6,042,540 A * | 3/2000 | Johnston | A61B 17/0206 600/219 |
| 6,206,826 B1 | 3/2001 | Matthews | |
| 6,468,207 B1 | 10/2002 | Fowler | |
| 6,733,444 B2 | 5/2004 | Phillips | |
| 6,860,850 B2 | 3/2005 | Phillips et al. | |
| 6,887,198 B2 * | 5/2005 | Phillips | A61B 17/0206 600/227 |
| 7,182,731 B2 | 2/2007 | Nguyen et al. | |
| 7,569,014 B2 | 8/2009 | Bass et al. | |
| 7,785,254 B2 * | 8/2010 | Teasdale | A61B 17/02 600/233 |
| 7,892,174 B2 | 2/2011 | Hestad et al. | |
| 8,114,020 B2 | 2/2012 | Fricke et al. | |
| 8,257,255 B2 | 9/2012 | Farley et al. | |
| 8,357,087 B2 | 1/2013 | Fetzer | |
| 8,360,971 B2 * | 1/2013 | Farley | A61B 17/02 600/215 |
| 8,808,176 B2 * | 8/2014 | Menendez | A61B 17/02 600/230 |
| 8,974,381 B1 | 3/2015 | Lovell et al. | |
| 9,044,280 B1 * | 6/2015 | Arambula | A61B 17/0293 |
| 9,113,853 B1 * | 8/2015 | Casey | A61F 2/447 |
| 9,216,016 B2 | 12/2015 | Fiechter et al. | |
| 9,277,906 B2 * | 3/2016 | White | A61B 17/02 |
| 9,320,506 B2 | 4/2016 | Bertagnoli et al. | |
| 9,386,916 B2 | 7/2016 | Predick et al. | |
| 9,510,812 B2 * | 12/2016 | Brown | A61B 17/02 |
| 2002/0026101 A1 | 2/2002 | Bookwalter et al. | |
| 2002/0095071 A1 | 7/2002 | Farley | |
| 2003/0004401 A1 | 1/2003 | Ball et al. | |
| 2003/0069478 A1 | 4/2003 | Phillips et al. | |
| 2004/0129109 A1 | 7/2004 | Phillips et al. | |
| 2004/0199055 A1 | 10/2004 | Mulac et al. | |
| 2004/0249388 A1 | 12/2004 | Michelson | |
| 2005/0113645 A1 | 5/2005 | Sharratt et al. | |
| 2005/0177028 A1 | 8/2005 | Royce et al. | |
| 2005/0192484 A1 | 9/2005 | Sharratt et al. | |
| 2005/0215865 A1 | 9/2005 | LeVahn et al. | |
| 2006/0224044 A1 | 10/2006 | Marchek et al. | |
| 2007/0270840 A1 | 11/2007 | Chin et al. | |
| 2008/0215081 A1 | 9/2008 | Hsueh et al. | |
| 2009/0221876 A1 | 9/2009 | Cobb et al. | |
| 2010/0256454 A1 | 10/2010 | Farley et al. | |
| 2015/0182211 A1 | 7/2015 | Nowak et al. | |
| 2018/0116758 A1 * | 5/2018 | Schlosser | F16M 13/022 |
| 2018/0271509 A1 * | 9/2018 | Truckey | A61B 17/0206 |
| 2019/0008498 A1 * | 1/2019 | McClymont | A61B 90/92 |
| 2020/0214686 A1 | 7/2020 | Truckey et al. | |
| 2021/0038211 A1 * | 2/2021 | Jouan | A61B 90/57 |

FOREIGN PATENT DOCUMENTS

| | | |
|---|---|---|
| FR | 2690067 | 10/1993 |
| FR | 2807313 | 10/2001 |
| GB | 1570499 | 7/1980 |

OTHER PUBLICATIONS

International Search Report and Written Opinion for PCT/US2018/047164, dated Nov. 9, 2018, 21 pages.

Patent Cooperation Treaty, Notification of Transmittal of the International Search Report and the Written Opinion of the International Searching Authority, in International Application No. PCT/US2011/040662, dated Oct. 11, 2011.

* cited by examiner

RETRACTOR SYSTEM AND RETRACTOR ARM WITH DETACHABLE HANDLE

BACKGROUND

The present disclosure relates to a surgical apparatus that retracts soft tissue and other anatomy of a patient in order to provide access to an operative site.

During a surgical procedure, a surgeon may make an incision in a patient to access internal organs, bones, and/or other anatomical structures. Retraction devices may be used to hold back soft tissue and other patient anatomy in the immediate area of the incision. Such retraction devices may provide the surgeon with an unobstructed view of the internal organs, bones, and/or other anatomical structures. Furthermore, the retraction devices may provide the surgeon with an opening via which the surgeon may access the anatomical structures with one or more surgical tools.

Further limitations and disadvantages of conventional and traditional approaches will become apparent to one of skill in the art, through comparison of such approaches with the present disclosure as set forth in the remainder of the present application with reference to the drawings.

SUMMARY

Various aspects of this disclosure provide a retractor system comprising retractor blades that retract anatomy to provide exposure of an operative site. For example and without limitation, various aspects of this disclosure are directed to a retractor system with one or more articulating arms to which retractor blades are attached. The articulating arms may position retractor blades in a surgical site and retain the retractor blades in a desired position. Detachable handles may be attached to the articulating arms to aid in positioning the articulating arms and/or retractor blades attached therefore. After positioning the articulating arms and/or retractor blades, the handle may be detached and removed in order to provide less encumbered access to the surgical site.

DETAILED DESCRIPTION

Figure 1:
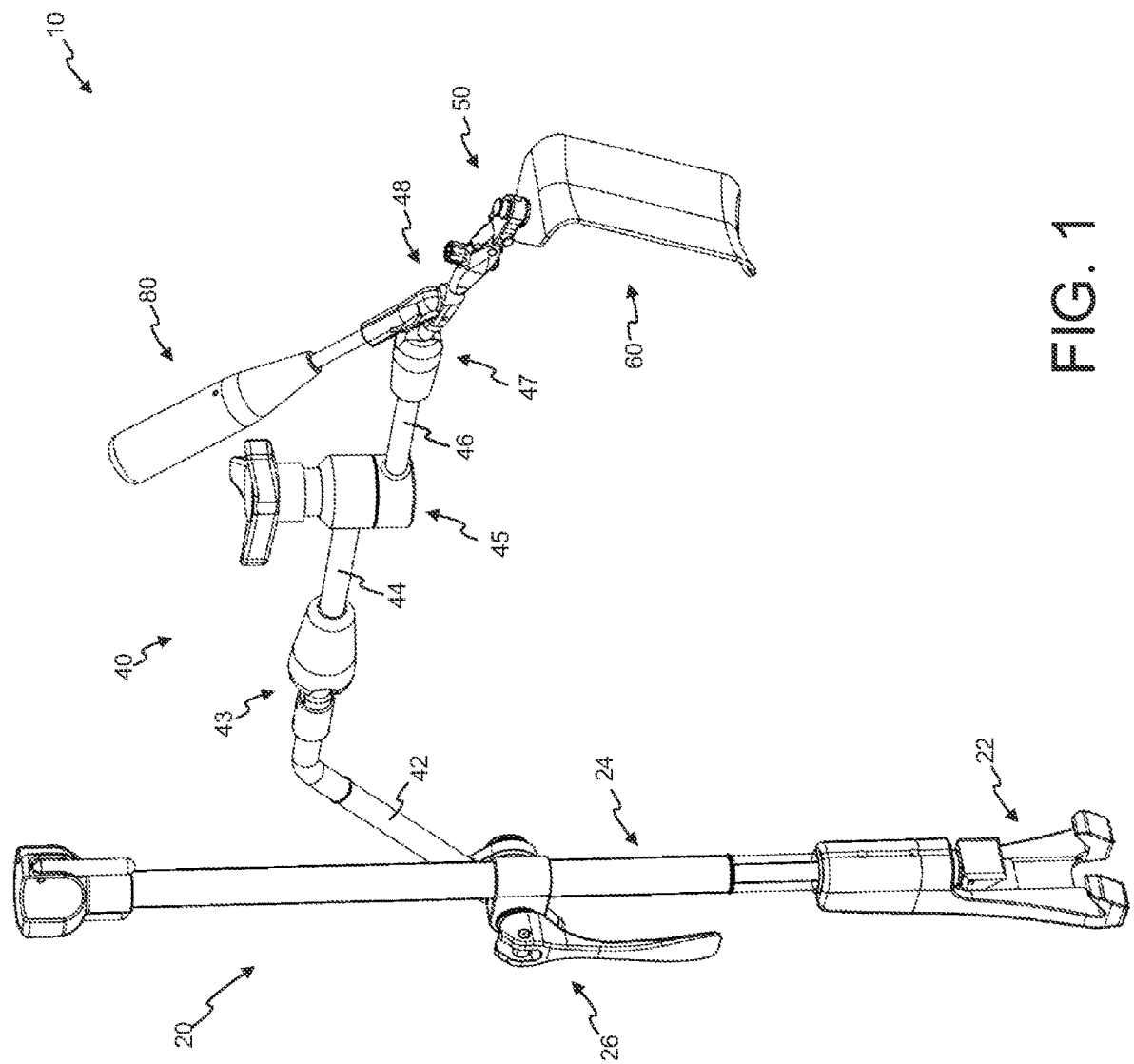
FIG. 1 provides a perspective view of a retractor system in accordance with various aspects of the present disclosure.

The following discussion presents various aspects of the present disclosure by providing examples thereof. Such examples are non-limiting, and thus the scope of various aspects of the present disclosure should not necessarily be limited by any particular characteristics of the provided examples. In the following discussion, the phrases "for example," "e.g.," and "exemplary" are non-limiting and are generally synonymous with "by way of example and not limitation," "for example and not limitation," and the like.

As utilized herein, "and/or" means any one or more of the items in the list joined by "and/or". As an example, "x and/or y" means any element of the three-element set $\{(x), (y), (x, y)\}$. In other words, "x and/or y" means "one or both of x and y." As another example, "x, y, and/or z" means any element of the seven-element set $\{(x), (y), (z), (x, y), (x, z), (y, z), (x, y, z)\}$. In other words, "x, y and/or z" means "one or more of x, y, and z."

The terminology used herein is for the purpose of describing particular examples only and is not intended to be limiting of the disclosure. As used herein, the singular forms are intended to include the plural forms as well, unless the context clearly indicates otherwise. It will be further understood that the terms "comprises," "includes," "comprising," "including," "has," "have," "having," and the like when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. may be used herein to describe various elements, these elements should not be limited by these terms. These terms are only used to distinguish one element from another element. Thus, for example, a first element, a first component, or a first section discussed below could be termed a second element, a second component, or a second section without departing from the teachings of the present disclosure. Similarly, various spatial terms, such as "upper," "lower," "side," and the like, may be used in distinguishing one element from another element in a relative manner. It should be understood, however, that components may be oriented in different manners, for example a device may be turned sideways so that its "top" side is facing horizontally and its "side" side is facing vertically, without departing from the teachings of the present disclosure. Additionally, the term "on" will be utilized in the document to mean both "on" and "directly on" (e.g., with no intervening component).

In the drawings, various dimensions (e.g., thicknesses, widths, etc.) may be exaggerated for illustrative clarity. Additionally, like reference numbers are utilized to refer to like elements through the discussions of various examples.

The discussion will now refer to various example illustrations provided to enhance the understanding of the various aspects of the present disclosure. The scope of this disclosure is not limited by specific characteristics of the examples provided and discussed herein.

FIG. 1 illustrates an embodiment of a retractor system 10 in accordance with various aspects of the present disclosure. The retractor system 10 may include a mounting assembly 20, an articulated arm 40, a retractor blade 60, and a handle 80. In particular, FIG. 1 depicts a single mounting assembly 20 with a single articulated arm 40 attached to the mounting assembly 20. However, in some embodiments, the retractor system 10 may include a different number of mounting assemblies 20 and/or a different number of articulated arms 40 attached to each mounting assembly 20.

As further shown, the retractor system 10 may include a retractor blade 60 and a handle 80 attached to each articulated arm 40. However, in some embodiments, the retractor system 10 may include a different number of handles 80 and/or a different number of retractor blades 60. For example, a person may use the handle 80 to position one articulated arm 40 and then detach the handle 80 from the positioned articulated arm 40. The person may then attach the handle 80 to another articulated arm 40 and use the newly attached handle 80 to position the another articulated arm 40.

Each mounting assembly 20 may include a bed mount 22, a post 24, and a clamp 26. In particular, the bed mount 22 of each mounting assembly 20 may affix a respective post 24 to a hospital bed (not shown). In particular, the post 24 may be affixed such that the post 24 extends upward from the bed mount 22 in a generally vertical direction. Each post 24 may provide a location to which a person may secure an articulated arm 40. In particular, the articulated arm 40 may be affixed to the post 24 via the clamp 26. When its handle is in a released position, the clamp 26 may slide along the length of the post 24 and adjust a height of the articulated arm 40. Moreover, the clamp 26 may permit a length of the articulated arm 40 to slide through the clamp 26 and effectively adjust a distance that a distal end of the articulated arm 40 is from the post 24. After appropriately adjusting the height and length of the articulated arm 40, the handle of clamp 26 may be moved to a locked position. In the locked position, the clamp may secure the articulated arm 40 to the post 24, prevent further sliding of the clamp 26 along the post 24, and prevent further sliding of the articulated arm 40 through the clamp 26.

Each articulated arm 40 is adapted to adjustably constrain a retractor blade 60 secured to the distal end of the articulated arm 40. In some embodiments, the articulated arm 40 may provide the retractor blade 60 with at least some freedom of movement relative to the post 24 and the bed mount 22. In particular, the articulated arm 40 may allow the retractor blade 60 some limited movement but may generally maintain the retractor blade 60 at or near a selected position. In other embodiments, the articulated arm 40 may be adapted to maintain the retractor blade 60 in a substantially fixed or stationary position once the articulated arm 40 is positioned and locked into place.

To this end, the articulated arm 40 may comprise multiple arm segments and joints that permit articulating the arm segments. In particular, the articulated arm 40 may include a shoulder arm segment 42. A distal end of the shoulder arm segment 42 may be joined to a proximal end of an upper arm segment 44 by a should joint 43. Moreover, a distal end of the upper arm segment 44 may be joined to a proximal end of a fore arm segment 46 by an elbow joint 45. Finally, a distal end of the fore arm segment 46 may be joined to a proximal end of a handle arm segment 48 by a wrist joint 47.

The arm segments 42, 44, and 46 are generally referred to herein as a "shoulder" arm segment, an "upper" arm segment, a "fore" arm segment in a manner similar to a human arm. Similarly, joints 43, 45, 47 are generally referred to herein as a "shoulder" joint, an "elbow" joint, and a "wrist" joint in a manner similar to joints of a human arm. However, such terms are merely used as a manner of convenience. This analogy to a human arm is especially helpful with regard to the depicted embodiment in which the joints 43, 47 are ball joints and the joint 45 is a pivot joint. Such joints provide the articulated arm 40 with articulation similar to the human arm. However, the articulated arm 40, in some embodiments, may include a fewer number of arm segments or a greater number of arm segments. Similarly, the joints of the articulated arm 40 may not align with joints of the human arm and may comprise some combination of single-axis hinge joints, pivot joints, universal joints, ball joints, prismatic joints, and/or other types of joints.

The arm segments 44, 46, 48 may each comprise one or more generally straight and generally cylindrical members. Similarly, the shoulder arm segment 42 may include one or more generally cylindrical members. However, unlike arm segments 44, 46, 48, the cylindrical members of the shoulder arm segment 42 may include one or more bends or curves. In some embodiments, the arm segment 42, 44, 46, 48 may each comprise various straight and/or bent members so as to accommodate different procedures or access sites.

Figure 2A:
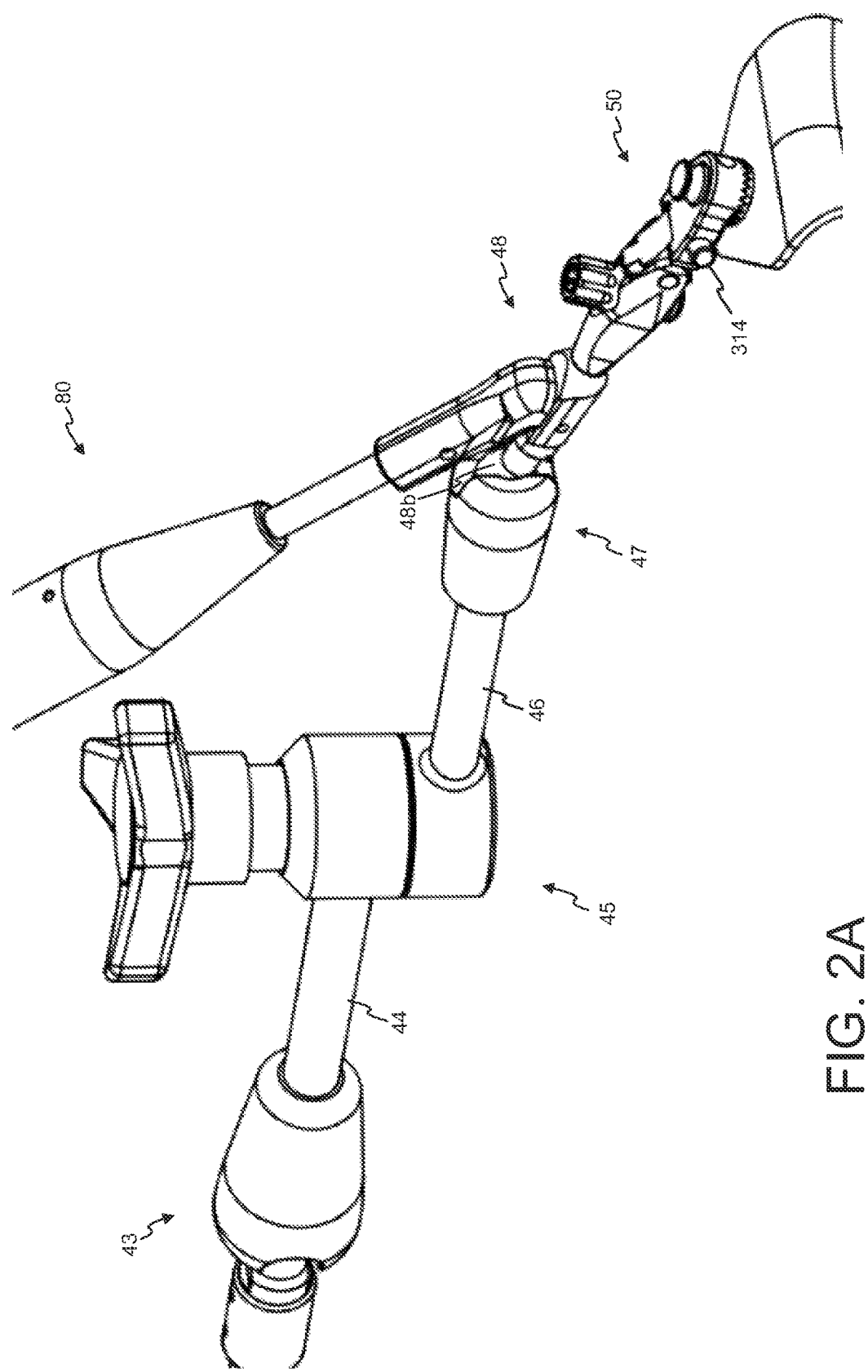
FIGS. 2A and 2B provide further perspective views of the retractor system of FIG. 1.
Figure 2B:
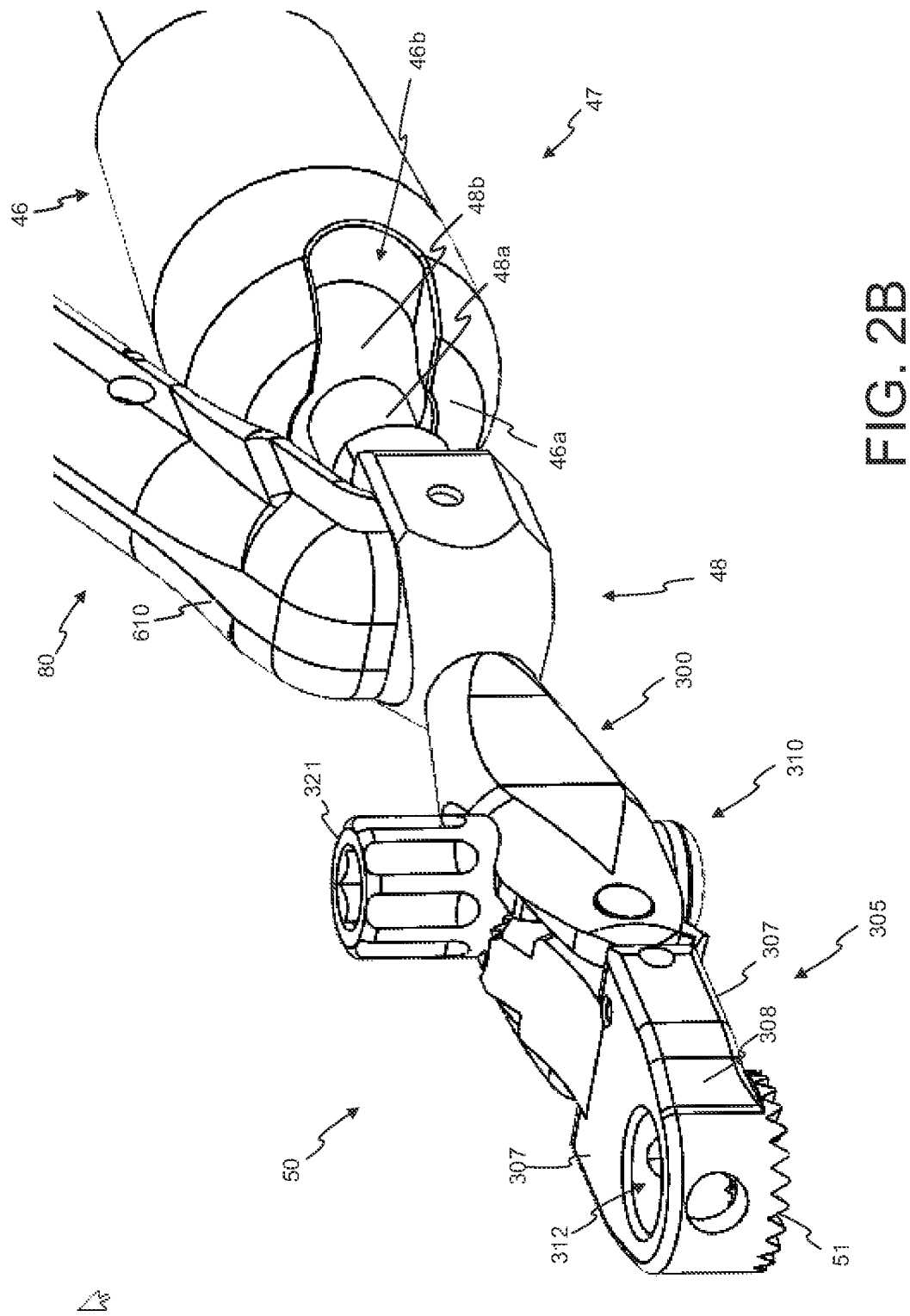

As shown in FIGS. 2A and 2B, the fore arm segment 46 and handle arm segment 48 are joined by the wrist joint 47. In particular, a distal end of the fore arm segment 46 may include a socket 46a of the wrist joint 47. Moreover, a proximal end of the handle arm segment 48 may include a shaft 48a, which is coupled to a ball 48b of the wrist joint 47. However, in other embodiments, the proximal end of the handle arm segment 48 may include the socket of the wrist joint 47 and the distal end of the fore arm segment 46 may include a shaft attached to a ball of the wrist joint 47.

In general, the ball 48b may engage internal sides of the socket 46a and the socket 46a may prevent the ball 48b from being withdrawn from socket 46a. However, the socket 46a may otherwise permit the ball 48b to rotate within the socket 46a and along the internal sides of the socket 46a. As such, the wrist joint 47 may permit articulation of the handle arm segment 48 with respect to the fore arm segment 46 about multiple axes or an indefinite number axes. In some embodiments, the wrist joint 47 may constrain or otherwise limit a degree of movement of the handle arm segment 48 about one or more axes. For example, as shown in FIG. 2B, the wrist joint 47 may be oriented such that an opening 46b of the socket 46a is narrower in the vertical direction than in the horizontal direction. In such an embodiment, upper and lower sides of the socket opening 46b may engage the shaft 48a and limit articulation of the handle arm segment 48 in an upward or downward direction. Conversely, left and right sides of the socket opening 46b may engage the shaft 48a and limit articulation of the handle arm segment 48 in a leftward or rightward direction, but permit greater articulation in such directions than what is permitted in the upward or downward directions.

FIG. 2A depicts an orientation of the wrist joint 47 in which the socket opening 46b permits greater articulation in the vertical direction than in the horizontal direction. FIG. 2A further depicts that the shoulder joint 43 may be implemented in a manner similar to the wrist joint 47. In particular, FIG. 2A depicts an orientation of the shoulder joint 43 in which the socket opening of the shoulder joint 43 permits greater articulation in the horizontal direction than in the vertical direction.

Figure 3A:
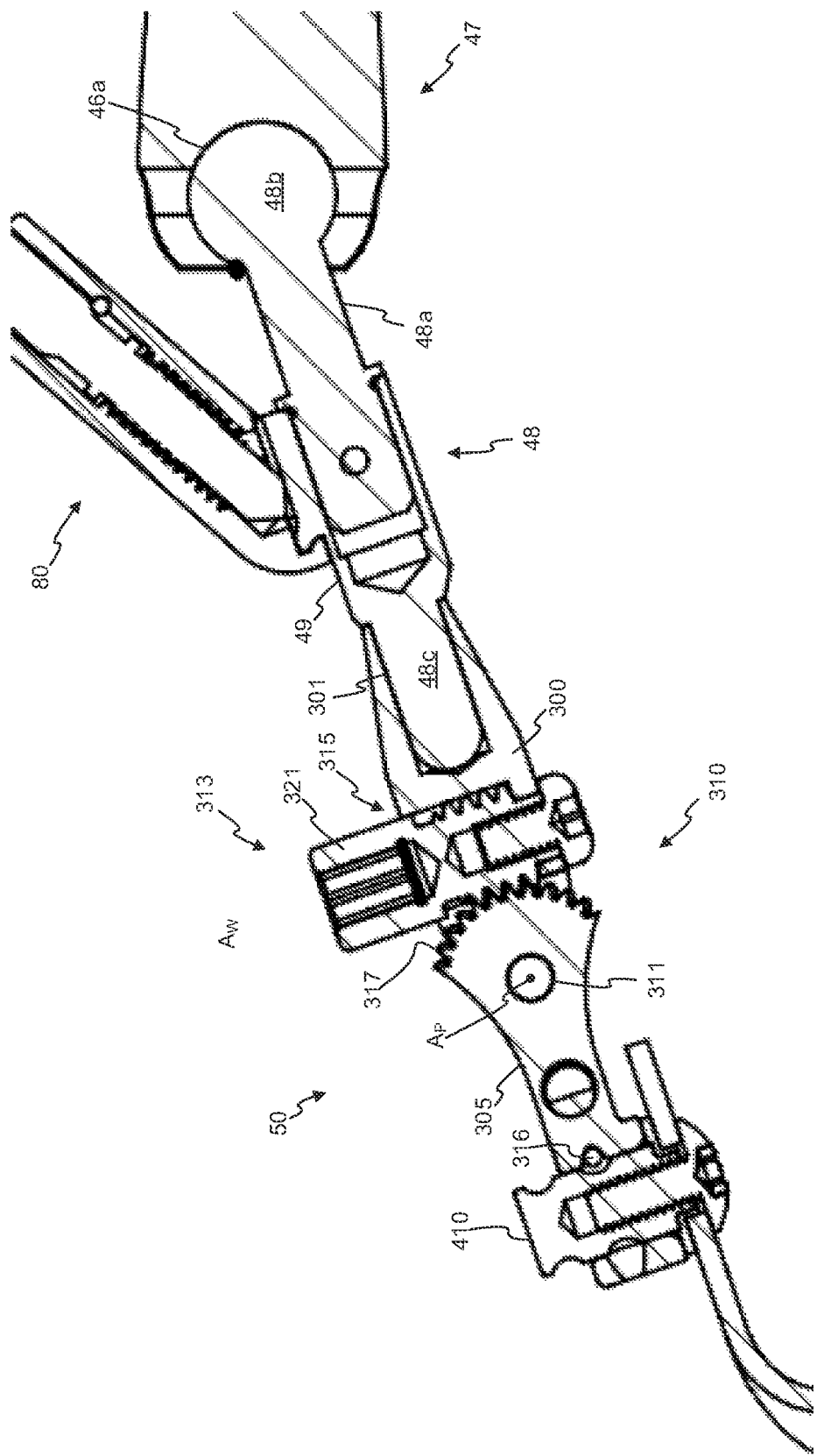
FIG. 3A provides a cross section view of the retractor connector, handle arm segment, and handle attached to a handle arm segment of FIG. 1.
Figure 3B:
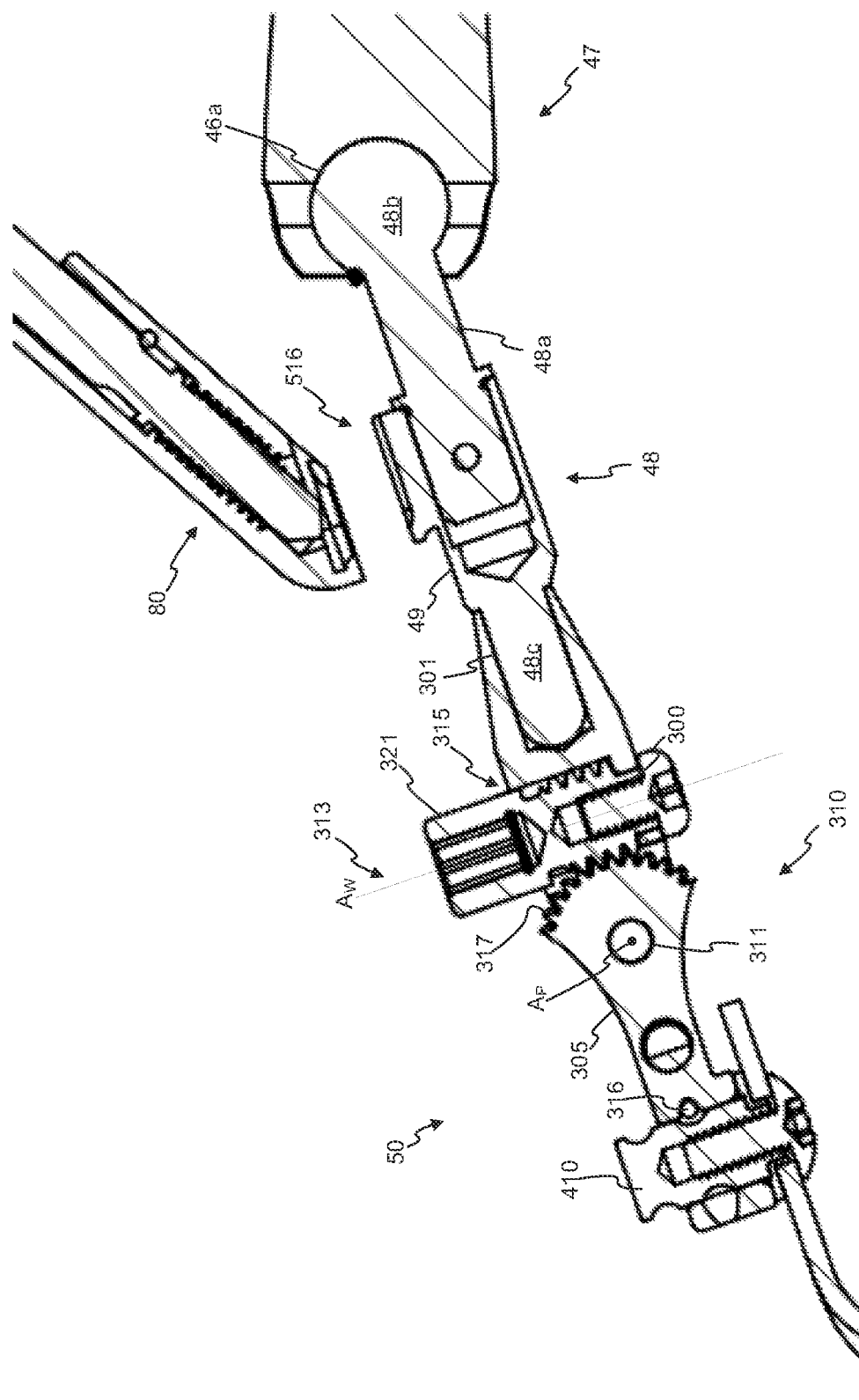
FIG. 3B provides a cross section view of the retractor connector, handle arm segment, and the handle detached from the handle arm segment of FIG. 1.

As shown, in FIGS. 3A and 3B, the retractor connector 50 may be at a distal end of the handle arm segment 48. The retractor connector 50 may comprise a connector body 300, a connector head 305, and an adjustable pivot 310. In particular, as shown in FIG. 3A, a cylindrical post 48c at the distal end of the handle arm segment 48 may be received by and affixed to a cylindrical port 301 at a proximal end of a connector body 300. Furthermore, a distal end of the connector body 300 may be coupled to a proximal end of the connector head 305 via the adjustable pivot 310.

The adjustable pivot 310 may comprise a pin 311 that passes through aligned barrel holes of connector body 300 and the connector head 305. The adjustable pivot 310 may further comprise a worm drive 313. The worm drive 313 may control and adjust the amount of pivot or angle between the connector body 300 and the connector head 305. In particular, a thumb screw or worm 315 of the worm drive 313 may pass through a distal end of the connector body 300 such that a longitudinal axis Aw of the worm 315 is perpendicular to the longitudinal axis $A_P$ of the pin 311. Furthermore, a worm gear 317 of the worm drive 313 may be positioned along a proximal end of the connector head 305 such that teeth of the worm gear 317 mesh with threads of the thumb screw or worm 315. Rotation of the worm 315 via the worm head 321 in a first direction may adjust or force the connector head 305 in a downward direction with respect to the connector body 300. Conversely, rotation of the worm 315 in a second direction opposite the first direction may adjust or force the connector head 305 in an upward direction with respect to the connector body 300.

The connector head 305 may include an upper side 306, a lower side 307, and sidewalls 308 that coupled the upper side 306 to the lower side 307. The connector head 305 may further include an attachment port 312 through the upper side 306 and the lower side 307, a release button 314, and a locking ball 316. In the illustrated embodiment, the attachment port 312 (FIG. 2B), release button 314 (FIG. 2A), and locking ball 316 (FIG. 3A) cooperate to detachably couple and lock a retractor blade 60 to the articulated arm 40. Through the use of an internal mechanism (not shown), depressing the release button 314 allows increased movement of the locking ball 316, which permits an attachment post 410 of retractor blade 60 to be inserted into or removed from the attachment port 312. Releasing the release button 314 causes the release button 314 and internal mechanism to return to a locked position in which the internal mechanism forces the locking ball 316 into the attachment port 312 such that the locking ball 316 engages the attachment post 410 of the retractor blade 60 and secures the retractor blade 60 to the retractor connector 50. Thus, a retractor blade 60 may be secured to the articulated arm 40 and a hospital bed via a retractor connector 50.

Figure 5:
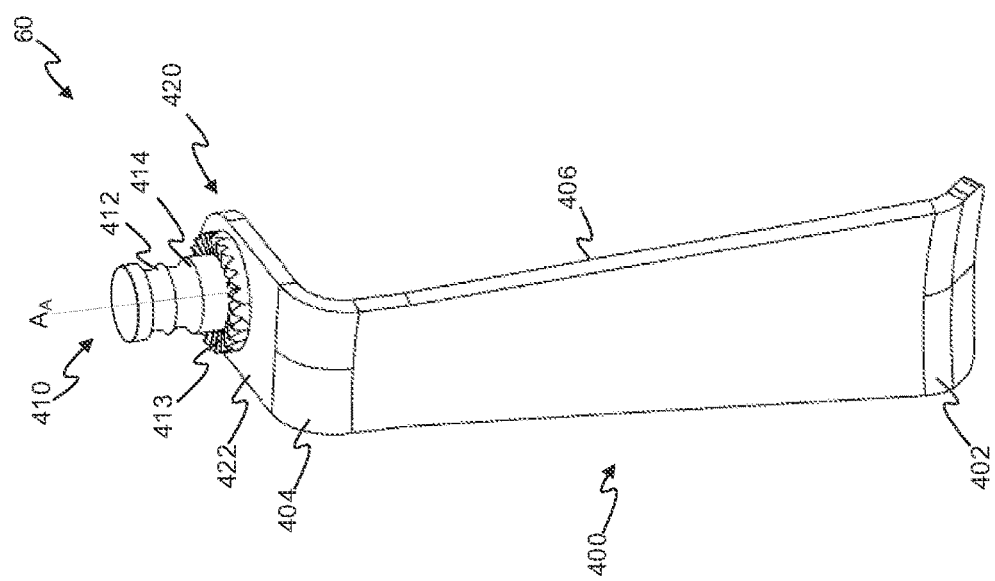
FIG. 5 provides a perspective view of a retractor blade and its attachment post suitable for use with the retractor system of FIG. 1.

Referring now to FIG. 5, the illustrated retractor blade 60 includes a blade 400 having a distal end 402, a proximal end 404, and a retracting portion 406. The retractor blade 60 may further include a base portion 420 having an attachment post 410. The distal end 402 may correspond to the end of the blade 400 oriented more deeply inside the patient during a surgical procedure, and the proximal end 404 may correspond to the end of the blade 400 oriented closer to a practitioner during a surgical procedure.

The retracting portion 406 generally extends from the proximal end 404 adjoined to the base portion 420 to the distal end 402. The retracting portion 406 may extend at an angle (e.g., 90°) from the base portion 420. The retracting portion 406 may be sized and adapted to hold back tissue from a site of interest during a procedure. In certain embodiments, the retractor system 10 may include a number of differently sized and/or shaped retractor blades 60 to provide increased adaptability for different procedures and/or patients.

The base portion 420, located proximate to the proximal end 404 of blade 400, may provide a location or locations to grasp and/or secure the retractor blade 60. Located proximate to the base portion 420 is the attachment post 410. The attachment post 410 may be sized and adapted to provide a location for attachment to connector head 305 of the retractor connector 50. In particular, the attachment post 410 may be sized and adapted to cooperate with the attachment port 312 of the retractor connector 50. To this end, the attachment post 410 may have a generally cylindrical-shape and may extend from an upper side 422 of the base portion 420. In one embodiment, a longitudinal axis AA of the attachment post 410 extends at a right angle from the upper side 422 of the retractor blade 60. However, the attachment post 410 in some embodiments may extend from the upper side 422 at other angles.

As shown in FIG. 5, the upper side 422 of the base portion 420 may include serrations or teeth 413. Similarly, as shown in FIG. 2B, a lower side of the retractor connector 50 may include serrations or teeth 51. The teeth 413 of the retractor blade 60 may engage the teeth 51 of the connector head 305 of the retractor connector 50 when the lower annular groove 414 accepts the locking ball 316. The engaged teeth 51, 413 may restrict rotation of the attachment post 410 relative to the connector head 305.

As shown in FIG. 5, the attachment post 410 may include an upper annular groove 412 and a lower annular groove 414. The attachment post 410 and annular grooves 412, 414 may be sized such that the attachment post 410 may pass freely through the attachment port 312 of the retractor connector 50 when the locking ball 316 of the retractor connector 50 is not placed into a locked position by the internal mechanism. However, when the release button 314 permits the internal mechanism to return to a locked position, the locking ball 316 is forced into the attachment port 312 and engages one of annular grooves 412, 414.

In particular, the upper annular groove 412 may be sized and adapted such that when the upper annular groove 412 is engaged with the locking ball 316 in the locked position, the attachment post 410 is prevented from moving longitudinally through the attachment port 312. However, when locking ball 316 engages the upper annular groove 412, the upper annular groove 412 may position the upper side 422 away from a lower side of the retractor connector 50. thus disengaging the teeth 51 of the retractor connector 50 from the teeth 413 of the retractor blade 60. Thus, with the locking ball 316 engaged with the upper annular groove 412, the attachment post 410 and attached blade 400 may rotate about the longitudinal axis AA with respect to the retractor connector 50.

Similar to the upper annular groove 412, the lower annular groove 414 may be sized and adapted such that when the lower annular groove 414 is engaged with the locking ball 316 in the locked position, the attachment post 410 is prevented from moving longitudinally through the attachment port 312. However, when locking ball 316 engages the lower annular groove 414, the lower annular groove 414 may position the upper side 422 of the retractor blade 60 such that the teeth 413 of the retractor connector 50 engage the teeth 413 of the retractor blade 60. Thus, with the locking ball 316 engaged with the lower annular groove 412, the engaged teeth 51, 413 may prevent the attachment post 410 and attached blade 400 from rotating about the longitudinal axis AA with respect to the retractor connector 50. Thus, by positioning the attachment post 410 such that the locking ball 316 engages either the upper annular groove 412 or the lower annular groove 414, a person may alter the amount of freedom of movement of the retractor blade 60 relative to the retractor connector 50.

In the depicted embodiments, the attachment port 312 of the retractor connector 50 and the attachment post 410 of the retractor blade 60 are cylindrical with circular cross-sections. Such an embodiment may permit swiveling of the retractor blade 60 with regard to the retractor connector 50, even after attachment. However, such swiveling of the retractor blade 60 may not be required or may not be desired for certain surgical procedures. As such, the attachment port 312 and the attachment post 410 may be shaped in a manner that prevents such swiveling. For example, the attachment port 312 and the attachment post 410 may remain cylindrical but have a non-circular cross-section (e.g., square, rectangular, hexagonal, etc.). In yet other embodiments, the attachment port 312 and attachment post 410 may not by cylindrical, but may otherwise provide a mating engagement of the retractor blade 60 to the retractor connector 50. For example, the attachment post 410 of the retractor blade 60 may be implemented as one or tabs and the attachment port 312 of the retractor connector 50 may be implemented as one or more slots that are adapted to receive one or more tabs of the retractor blade 60. Furthermore, in some embodiments, the retractor connector 50 may include one or more openings (not shown) in sidewalls 308 of the retractor connector to permit a sideways loading the attachment post 410 into the attachment port 312 through one or such openings in the sidewalls 308.

As shown in FIG. 3B, the handle arm segment 48 may include a handle mount 516. The handle mount 516 may be sized and adapted to provide a location for attachment of the handle 80. A person may use the attached handle 80 to position the articulated arm 40 and a retractor blade 60 attached thereto.

Figure 6:
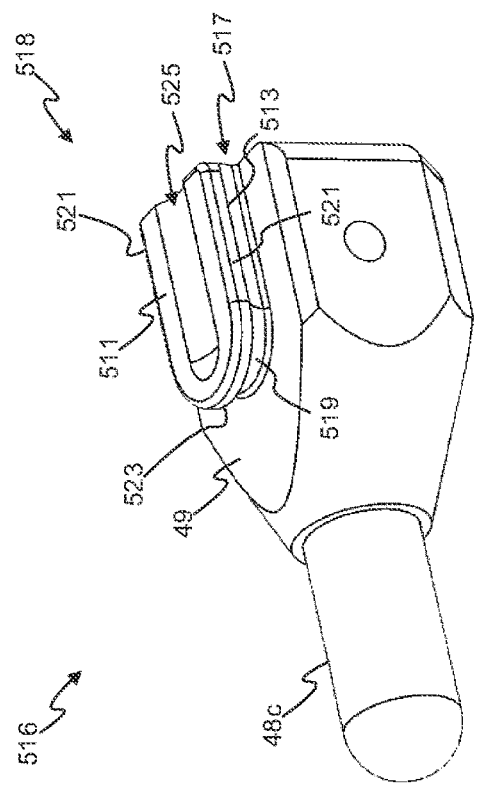
FIG. 6 provides a detailed perspective view of the handle mount of the handle arm segment.

Referring to FIG. 6, the handle mount 516 may comprise a generally, flat tab 518 having an upper side 511 and a lower side 513 that both extend parallel to an upper side 49 of the handle arm segment 48. A pedestal 519 may affix the lower side 513 of the tab 518 to the upper side 49 of the handle arm segment 48. In particular, the pedestal 519 may have a smaller width and length than the tab 518 such that lateral sides 521 and a distal end 523 of the tab 518 extend beyond the pedestal 519.

The tab 518 on the pedestal 519 may therefore define grooves 517 between the lower side 513 of the tab 518 and the upper side 49 of the handle arm segment 48. In particular, the grooves 517 may traverse along the lateral sides 521 of the tab 518 and may traverse parallel along the upper side 49 of the handle arm segment 48. As explained below, the handle 80 may be detachably coupled to the handle arm segment 48 via a slidable engagement of the handle 80 along the grooves 517. To this end, the distal end 523 of the tab 518 may be rounded or tapered to ease insertion of the tab 518 into an attachment portion 610 of the handle 80. Furthermore, the upper side 511 of the tab 518 may include a tab recess 525. The tab recess 525 is sized to receive a rod 660 of the handle 80. When received, the rod 660 may be advanced to a locked position in which the rod engage walls of the tab recess 525 and prevents removal of the tab 518 from the attachment portion 610 of the handle 80. Thus, when advanced to the locked position, the rod 660 may lock the handle 80 to the handle arm segment 48.

In the depicted embodiments, the lateral sides 521 of the tab 518 are aligned or parallel with a longitudinal axis of the handle arm segment 48. However, in some embodiments, the lateral sides 521 may be aligned perpendicular to or at some other angle with regard to the longitudinal axis of the handle arm segment 38. Moreover, the handle mount 516 is depicted attached to an upper surface of the handle arm segment 48 with upper and lower sides 511, 513 parallel with the upper surface of the handle arm segment 48. However, in some embodiment the handle mount 516 may be attached to other surfaces of the handle arm segment 48 and/or at an angle with regard to the attached surface. The angle and/or surface to which the handle mount 516 is attached may be adjusted to better accommodate forces applied to the attached handle 80 for various procedures. Furthermore, the tab 518 may have other shapes such as circular, oval, etc. which may accommodate attaching the handle 80 from multiple angles.

Figure 4B:
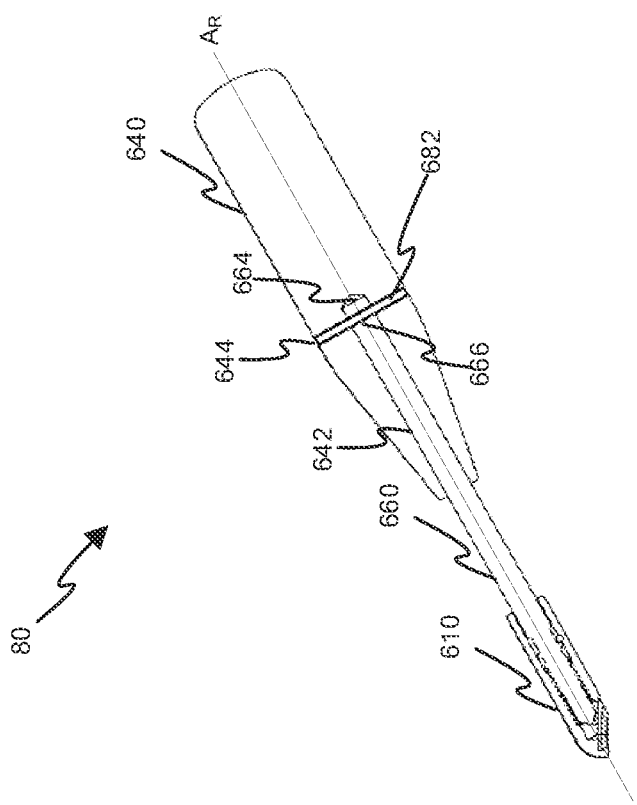
FIGS. 4A-4C depicted various details of the handle of the retractor system of FIG. 1.
Figure 4A:
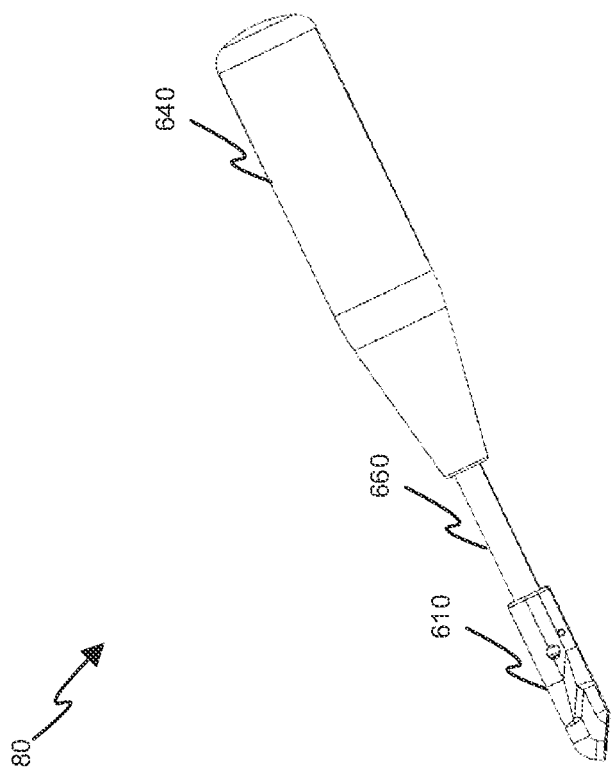
Figure 4C:
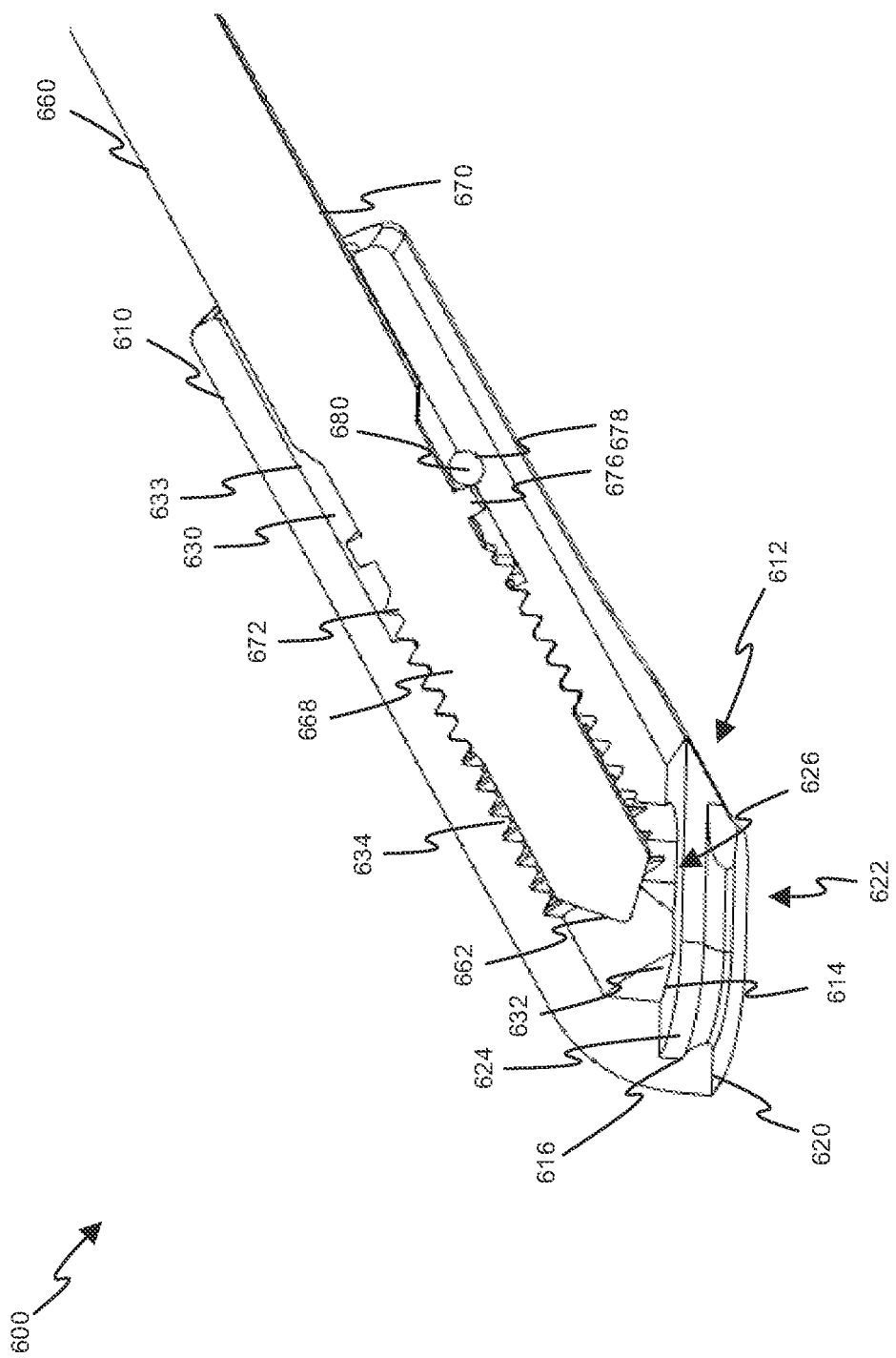

Referring not to FIGS. 4A-4C, the handle 80 may include an attachment portion 610, a hand grip 640, and a rod 660. The rod 660 may secure the hand grip 640 to the attachment portion 610. Moreover, the rod 660 may be manipulated to selectably engage the rod 660 with the walls of the tab recess 525.

The attachment portion 610 may be sized and adapted to cooperate with the handle mount 516 of the handle arm segment 48. The attachment portion 610 may comprise a slot 612 that is sized and adapted to accept and mate with the tab 518 and grooves 517 of the handle mount 516. The slot 612 and tab 518 may cooperate to secure the attachment portion 610 to the handle arm segment 48. To this end, the slot 612 may comprise an upper side 614 and a lower side 616. The lower side 616 may be spaced apart from the upper side 614 by a distance slightly larger than a thickness of the tab 518 of the handle mount 516. In this manner, the tab 518 of the handle mount 516 may be received by the slot 612 such that the sides 614, 616 of the attachment portion 610 closely mate and engage the sides 511, 513 of the handle mount 516.

Furthermore, the lower side 616 of the slot 612 may include an opening 622 sized to receive and closely mate with the pedestal 519 upon which the tab 518 rests. The slot 612 may further comprise an end wall 624. The end wall 624 may be sized to receive and closely mate with the rounded or tapered distal end 523 of the tab 518. In particular, the end wall 624 and distal end 523 may cooperate to properly position the tab 518 within the slot 612. In particular, the end wall 624 may stop further advancement of the distal end 523 into the slot 612 when the tab recess 525 is properly aligned to receive the rod 660.

Finally, the upper side 614 of the slot 612 includes an aperture 626. In particular, the aperture 626 is positioned in the upper side 614 of the attachment portion 610 such that the aperture 626 aligns with the tab recess 525 when the tab 518 is fully inserted into the slot 612. The aperture 626 is sized to closely mate with a tip 662 of the rod 660. As shown, the tip 662 may be beveled or tapered. Such tapering may help guide the tip 662 into the tab recess 525 even in the presence of minor misalignment of the tab recess 525 with the aperture 626. For example, a person may fail to fully insert the tab 518 into the slot 612. The tapered tip 662 may aid the rod 660 in sliding into the tab recess 525 and urging the tab 518 into a fully inserted position.

As further shown, the attachment portion 610 may include a longitudinal cavity 630 that is sized and adapted to receive a threaded end 668 of the rod 660. As shown, a distal end 632 of the longitudinal cavity 630 may adjoin the aperture 626 positioned in the upper side 614 of the attachment portion 610. The longitudinal cavity 630 may be shaped and sized such that its inner walls 633 closely mate with side walls 670 of the rod 660 and permit the rod 660 to slide longitudinally along at least a portion of the longitudinal cavity 630. The inner walls 633 may include threads 634 toward the distal end 632. The threads 634 are configured to engage threads 672 of the rod 660.

As a result of such threads 634, 672, the rod 660 may be advanced through the longitudinal cavity 630 and into the aperture 626 positioned in the upper side 614 of the attachment portion 610 via rotation of the rod 660 in a first direction about a longitudinal axis $A_R$. Conversely, rotation of the rod 660 in a second direction opposite the first direction may withdrawal the rod 660 from the aperture 626.

With reference to FIGS. 3A and 4C, as the rod 660 is advanced into the aperture 626, a tapered end 632 of the rod 660 may engage the tab recess 525 of tab 518 and prevent withdrawal of the tab 518 from the attachment portion 610. Once in the locked position, an annular rib 676 of rod 660 clears an aperture 678 in the attachment portion 610 that extends laterally into the longitudinal cavity 630. A pin 680 may then be inserted into the aperture 678. The pin 680 may engage and block the passage of the annular rib 676 and thereby prevent withdrawal of the rod 660 from the aperture 626. In this manner, the rod 660 may be secured to the handle mount 516 of the handle arm segment 48 and thus prevent the detachment of the handle 80 from the handle arm segment 48.

The hand grip 640 may be sized and adapted to be grasped by a person. The hand grip 640 may include an aperture 642 sized to receive a proximal end 664 of the rod 660. As shown in FIG. 4B, the hand grip 640 may further include an aperture 644 which may be aligned with a corresponding aperture 666 toward the proximal end 664 of the rod 660. Another pin 682 may be passed through the apertures 644, 666 thereby locking the hand grip 640 to the rod 660. As such, a person may rotate the hand grip 640 about the longitudinal axis $A_R$ of the rod 660 in order to advance the rod 660 through the aperture 626.

After the handle 80 is secured to the handle arm segment 48, the hand grip 640 provides for convenient manipulation and placement of the articulated arm 40 and an attached retractor blade 60. After the articulated arm 40 and retractor blade 60 are positioned as desired, a person may remove the pin 680 from the attachment portion 610. The person may then rotate the hand grip 640 about longitudinal axis $A_R$ to withdrawal the rod 660 from the aperture 626 and disengage the rod 660 from the handle mount 516. After such disengagement, the handle 80 may be detached from the handle arm segment 48 by simply sliding the attachment portion 610 off the tab 518 of the handle mount 516.

The following provides an exemplary process for using the retractor system 10. The process may provide further insight regarding various aspects of the retractor system 10. However, the order of several of the steps is not rigid and various steps may be performed in a different order without deviating from the spirit and scope of the pending claims. The process may begin with securing the mounting assemblies 20 to the hospital bed before or after a patient is placed on the hospital bed. Similarly, articulated arms 40 may be secured to the mounting assemblies 20 before or after the mounting assemblies are secured to the hospital bed. A person may select a suitable retractor blade 60 and secure the retractor blade 60 to the blade connector 50 of an articulated arm 40. Furthermore, the attachment portion 610 of a handle 80 may be slid over a tab 518 of a handle mount 516 and then hand grip 640 may be rotated to advance the rod 660 and lock the handle 80 to the handle mount 516. The retractor blade 60 and articulated arm 40 may be manipulated with the aid of the attached handle 80 so as to insert a distal end of the retractor blade 60 into the operative site and position the retractor blade 60 and/or articulated arm 50 as desired to retract tissue and provide access to the surgical site of interest. After positioned as desired, the hand grip 640 may be rotated in the opposite direction so as to withdrawal the rod 660 and release the handle 80 from the handle mount 516. The attachment portion 610 of the released handle 80 may be slid off the tab 518 and removed from the handle mount 516. After removing the handle 80, the retractor blade 60 may be secured at both its distal end via the patient's anatomy and at proximal end via the articulated arm 40, thus removing the need for manual holding of the retractor blade 60 during the procedure.

Further, while the articulated arm 40 generally maintains the retractor blade 60 in position, the motion permitted by the joints of the articulated arm 40 and/or the interaction between the retractor connector 50 and the upper annular groove 412 (if the upper annular groove 412 is utilized) allows some amount of "float" for the retractor blade 60 relative to the hospital bed in the event of any pounding, chiseling, or other events that may cause portions of the anatomy or equipment to shift, helping to maintain a desired access shape as well as helping to reduce risk of any additional injury or trauma to the patient, as well as damage to any equipment, that may be caused by such a shift or movement. Additional retractor blades 60 and articulated arm 40 may be added, positioned, and secured in place in a similar manner. Thus, the retractor system 10 provides for flexibility in the formation of the desired access site, as well as, reducing obstacles to accessing the site of interest.

While particular embodiments of the invention have been shown, it will be understood that the invention is not limited thereto since modifications may be made by those skilled in the art, particularly in light of the foregoing teaching. It is therefore, the appended claims that define the true spirit and scope of the invention.

What is claimed is:

1. A retractor system, comprising:
an articulated arm comprising an articulated arm distal end, an articulated arm proximal end, a plurality of arm segments between the articulated arm distal end and the articulated arm proximal end, wherein an arm segment of the plurality of arm segments comprises a permanent handle mount adapted to detachably couple a handle to the articulated arm; and
a retractor connector that extends from the articulated arm distal end, the retractor connector adapted to couple a retractor blade to the articulated arm;
wherein the retractor connector comprises a connector body coupled to the articulated arm and a connector head coupled to the connector body via an adjustable pivot;
wherein the adjustable pivot comprises a worm gear and a worm drive engaged with the worm gear; and
wherein rotation of the worm gear adjusts an angle between the connector body and the connector head.

2. The retractor system of claim 1, comprising a plurality of joints that permit articulation of the plurality of arm segments.

3. The retractor system of claim 2, wherein a first joint of the plurality of joints comprises a ball of a first arm segment of the plurality of arm segments in a socket of a second arm segment of the plurality of arm segments.

4. The retractor system of claim 3, wherein the first joint comprises a socket opening that permits greater articulation in a first direction than in a second direction.

5. The retractor system of claim 1, wherein the handle mount comprises a tab and a pedestal that affixes the tab to the articulated arm.

6. The retractor system of claim 5, wherein the tab comprises:
a first lateral side;
a second lateral side parallel to the first lateral side; and
a tapered distal end that adjoins the first lateral side to the second lateral side.

7. The retractor system of claim 1, wherein:
the retractor connector comprises an attachment port;
the retractor system comprises the retractor blade with an attachment post;

the attachment post of the retractor blade comprises an annular groove;

the retractor connector engages the annular groove when the attachment post is received by the attachment port; and engagement of the annular groove by the retractor connector prevents withdraw of the attachment post from the attachment port.

8. The retractor system of claim 1, comprising a mounting assembly, wherein the mounting assembly comprises:

a post;

a bed mount configured to affix the post to a hospital bed; and a clamp configured to couple the articulated arm to the post.

9. The retractor system of claim 1, comprising the handle, wherein:

the handle comprises an attachment portion; and the attachment portion comprises a slot configured to receive the handle mount.

10. A retractor system, comprising:

an articulated arm comprising a handle mount adapted to detachably couple a handle to the articulated arm; and a retractor connector at a distal end of the articulated arm, the retractor connector adapted to couple a retractor blade to the articulated arm;

wherein the handle mount comprises:

a tab comprising a first lateral side, a second lateral side parallel to the first lateral side, and a tapered distal end that adjoins the first lateral side to the second lateral side;

a pedestal that affixes the tab to the articulated arm;

a first groove between a lower side of the tab and an upper side of the articulated arm, wherein the first groove traverses along the first lateral side of the tab; and a second groove between the lower side of the tab and the upper side of the articulated arm, wherein the second groove traverses along the second lateral side of the tab.

11. The retractor system of claim 10, comprising the handle, wherein:

the handle comprises an attachment portion and a rod;

the attachment portion comprises a slot configured to receive the tab of the handle mount;

the rod engages the tab of the handle mount and secures the handle to the handle mount when advanced through the attachment portion and into the slot; and the rod disengages the tab of the handle mount and permits withdrawing the tab from the attachment portion of the handle when withdrawn from the slot.

12. The retractor system of claim 11, wherein:

the tab of the handle mount comprises an upper side and a recess in the upper side of the tab; and the rod engages a side wall of the recess when the rod is advanced into the slot.

13. The retractor system of claim 11, wherein:

the attachment portion comprises threads along an inner wall;

the rod comprises threads configured to engage the threads of the attachment portion;

wherein rotation of the rod about a longitudinal axis in a first direction causes the threads of the attachment portion and the rod to advance the rod into the slot; and wherein rotation of the rod about the longitudinal axis in a second direction opposite the first direction causes the threads of the attachment portion and the rod to withdraw the rod from the slot.

14. The retractor system of claim 11, wherein:

the attachment portion of the handle comprises an aperture;

the rod comprises an annular rib that clears the aperture when the rod is fully advanced into the slot;

the handle comprises a pin adapted to be inserted into the aperture after the rod is fully advanced into the slot; and the pin engages the annular rib and prevents withdrawal of the rod from the slot when inserted into the aperture after the rod is fully advanced into the slot.

15. A retractor system, comprising:

a mounting assembly comprising a post and a bed mount;

an articulated arm comprising:

an upper arm segment comprising a proximal end and a distal end, wherein the proximal end of the upper arm segment is coupled to the post;

a fore arm segment comprising a proximal end and a distal end, wherein the proximal end of the fore arm segment is coupled to the distal end of the upper arm segment via a first joint; and a handle arm segment comprising a proximal end and a distal end, wherein the proximal end of the handle arm segment is coupled to the distal end of the fore arm segment via a second joint;

a retractor connector coupled to the distal end of the handle arm segment;

a retractor blade attached to the retractor connector; and a handle detachably secured to a handle mount protruding from a side surface of the handle arm segment proximal to the retractor blade.

16. The retractor system of claim 15, wherein:

the first joint permits articulation of the fore arm segment with regard to the upper arm segment; and the second joint permits articulation of the handle arm segment with regard to the fore arm segment.

17. The retractor system of claim 16, wherein:

the handle comprises an attachment portion and a rod;

the attachment portion comprises a slot configured to receive the handle mount and permit the handle mount to slide out of the slot when the rod is not in a locked position; and the rod engages the handle mount and prevents the handle mount from sliding out of the slot when the rod is in the locked position.

18. The retractor system of claim 15, wherein:

the handle mount comprises a tab and a pedestal that affixes the tab to the handle arm segment;

the handle comprises an attachment portion;

the attachment portion comprises a slot configured to receive the tab of the handle mount and permit the tab of the handle mount to slide out of the slot when the handle is not in a locked position;

the distal end of the fore arm segment comprises a socket of the second joint;

the proximal end of the handle arm segment comprises a ball of the second joint;

the ball of the handle arm segment engages internal sides of the socket of the fore arm segment; and an opening of the socket permits greater articulation of the handle arm segment with regard to the fore arm segment in a first direction than in a second direction.

* * * * *